US010762983B2

(12) United States Patent
Fewins et al.

(10) Patent No.: US 10,762,983 B2
(45) **Date of Patent: *Sep. 1, 2020**

(54) SELECTING ALTERNATE RESULTS FOR INTEGRATED DATA CAPTURE

(75) Inventors: Jon Fewins, Shawnee, KS (US); Ryan Moog, Olathe, KS (US); Marsha Laird-Maddox, Kansas City, MO (US); Todd Jeffrey Reynolds, Kansas City, MO (US); Brady Timmerberg, Kansas City, MO (US); Ross St. Clair, Gainesville, VA (US)

(73) Assignee: CERNER INNOVATION, INC., Lenexa, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/569,913

(22) Filed: Aug. 8, 2012

(65) Prior Publication Data

US 2014/0046687 A1 Feb. 13, 2014

(51) Int. Cl.

| | |
|---|---|
| ***G16H 10/20*** | (2018.01) |
| ***G06Q 50/24*** | (2012.01) |
| ***G16H 10/60*** | (2018.01) |

(52) U.S. Cl.

CPC ............. *G16H 10/20* (2018.01); *G06Q 50/24* (2013.01); *G16H 10/60* (2018.01)

(58) Field of Classification Search

CPC .. G06F 19/322; G06F 19/3487; G06F 3/0482; G06Q 50/22; G06Q 50/24

USPC .......................................................... 705/2, 3

See application file for complete search history.

(56) References Cited

U.S. PATENT DOCUMENTS

| | | | |
|---|---|---|---|
| 5,367,619 A | 11/1994 | Dipaolo et al. | |
| 5,737,539 A | 4/1998 | Edelson et al. | |
| 6,240,414 B1 * | 5/2001 | Beizer | G06F 17/30176 |
| 7,647,320 B2 | 1/2010 | Mok et al. | |
| 8,341,131 B2 * | 12/2012 | Cohen | G06F 17/30303 707/694 |
| 8,645,424 B2 | 2/2014 | Miller | |
| 8,738,396 B2 | 5/2014 | Green, III et al. | |
| 8,739,021 B2 | 5/2014 | Yuniardi | |
| 8,862,673 B2 | 10/2014 | Shkolnikov et al. | |
| 2003/0140044 A1 | 7/2003 | Mok et al. | |
| 2004/0049490 A1 * | 3/2004 | Milov | 707/1 |
| 2004/0128169 A1 | 7/2004 | Lusen | |
| 2004/0133450 A1 | 7/2004 | Foureaux et al. | |

(Continued)

OTHER PUBLICATIONS

First Action Interview Pre-Interview Communication dated Feb. 24, 2014 in U.S. Appl. No. 13/3569,961, 5 pages.

(Continued)

*Primary Examiner* — Jonathan Durant

(74) *Attorney, Agent, or Firm* — Shook, Hardy & Bacon LLP

(57) ABSTRACT

Systems, methods, computer-readable media, and graphical user interfaces for selecting alternate results for integrated data capture are provided. Integrated data capture workflows are initiated from within an electronic medical record (EMR). Data is gathered from the EMR to make available to a case report form. Case report forms are populated with the most recently collected values of data. Indicators are displayed if alternate results for items are available. Selections of indicators are received and closed menus of alternate results for the items are presented.

16 Claims, 13 Drawing Sheets

(56) References Cited

U.S. PATENT DOCUMENTS

2004/0220836 A1 11/2004 Doherty et al.
2005/0071194 A1* 3/2005 Bormann .......... G06F 17/30578 705/2
2005/0182658 A1 8/2005 Abraham-fuchs et al.
2005/0182664 A1 8/2005 Abraham-Fuchs et al.
2006/0036619 A1 2/2006 Fuerst et al.
2006/0293919 A1 12/2006 Morlet et al.
2008/0072209 A1* 3/2008 Farrah et al. ................. 717/113
2008/0133572 A1* 6/2008 Verhey-Henke ...... G06F 19/363
2009/0228303 A1* 9/2009 Faulkner ................ G06Q 50/24 705/3
2009/0281835 A1 11/2009 Patwardhan et al.
2010/0011078 A1* 1/2010 Shkolnikov et al. ......... 709/206
2010/0122210 A1 5/2010 Dogac et al.
2010/0305965 A1 12/2010 Benjamin et al.
2011/0054937 A1* 3/2011 Dibble .............................. 705/3
2011/0066955 A1* 3/2011 Olson et al. .................. 715/752
2011/0078608 A1 3/2011 Gannon et al.
2011/0125646 A1 5/2011 Yung
2011/0161101 A1 6/2011 Ikeguchi et al.
2011/0202370 A1* 8/2011 Green et al. ...................... 705/3
2011/0246216 A1 10/2011 Agrawal et al.
2011/0301982 A1 12/2011 Green, Jr. et al.
2012/0117457 A1* 5/2012 Yuniardi ....................... 715/229
2013/0080190 A1* 3/2013 Mansour ................ G06Q 10/10 705/3
2014/0047384 A1 2/2014 Fewins et al.
2014/0095204 A1 4/2014 Fung et al.
2014/0221858 A1 8/2014 Myr
2014/0222444 A1 8/2014 Cerello et al.
2017/0193194 A1 7/2017 Pillarisetty et al.
2017/0193195 A1 7/2017 Pillarisetty et al.

OTHER PUBLICATIONS

First Action Interview Office Action dated May 1, 2014 in U.S. Appl. No. 13/569,961, 14 pages.
Non-Final Office Action dated Oct. 16, 2014 in U.S. Appl. No. 13/569,961, 17 pages.
First Action Interview Pre-Interview Communication dated Oct. 20, 2014 in U.S. Appl. No. 13/569,932, 5 pages.
First Action Interview Pre-Interview Communication dated Nov. 21, 2014 in U.S. Appl. No. 13/569,976, 5 pages.
Non-Final Office Action dated Jan. 7, 2015 in U.S. Appl. No. 13/569,932, 19 pages.
Non-Final Office Action dated Aug. 13, 2015 in U.S. Appl. No. 13/569,932, 23 pages.
Non-Final Office Action dated Aug. 17, 2015 in U.S. Appl. No. 13/569,961, 24 pages.
Final Office Action dated Aug. 18, 2015 in U.S. Appl. No. 13/569,976, 15 pages.
First Action Interview Office Action dated Feb. 9, 2015 in U.S. Appl. No. 13/569,976, 3 pages.
Final Office Action dated Mar. 26, 2015 in U.S. Appl. No. 13/569,961, 19 pages.
Final Office Action dated May 1, 2015 in U.S. Appl. No. 13/569,932, 20 pages.
Non-Final Office Action dated Jun. 23, 2016 in U.S. Appl. No. 13/569,932. 28 pages.
Final Office Action dated Jan. 15, 2016 in U.S. Appl. No. 13/569,932, 24 pages.
Final Office Action dated Feb. 1, 2016 in U.S. Appl. No. 13/569,961, 30 pages.
Mon-Final Office Action dated Sep. 14, 2016 in U.S. Appl. No. 13/569,961, 29 pages.
Final Office Action dated Jan. 13, 2017 in U.S. Appl. No. 13/569,932, 30 pages.
Final Office Action dated Feb. 14, 2017 in U.S. Appl. No. 13/569,961, 29 pages.
Non-Final Office Action dated Jul. 27, 2017 in U.S. Appl. No. 13/569,932, 30 pages.
Non-Final Office Action dated Aug. 10, 2017 in U.S. Appl. No. 13/569,961, 29 pages.
Final Office Action of U.S. Appl. No. 13/569,932, dated Nov. 27, 2017, 31 pages.
Final Office Action of U.S. Appl. No. 13/569,961, dated Nov. 29, 2017, 29 pages.
First Action Interview received for U.S. Appl. No. 15/060,199, dated Dec. 10, 2019, 22 pages.
Preinterview First Office Action received for U.S. Appl. No. 15/060,191, dated May 17, 2019, 4 pages.
Preinterview First Office Action received for U.S. Appl. No. 15/060,199, dated Jul. 5, 2019, 4 pages.
Non-Final Office Action received for U.S. Appl. No. 13/569,961, dated Sep. 27, 2018, 35 pages.
Final Office Action received for U.S. Appl. No. 13/569,961, dated Jul. 9, 2019, 32 pages.
Final Office Action received for U.S. Appl. No. 15/060,199, dated May 11, 2020, 13 pages.

* cited by examiner

DATA COLLECTION EVENT

HELP   LOGOUT
LOGGED IN AS: #########

(i) EHR DATA AVAILABLE

PROTOCOL CODE: IDC_DEFAULT_STUDY        DATE RANGE FILTER: 06/15/2011        1004111

CONMED
SHOW/HIDE ANNOTATION ~902

CONMED

| | NAME OF THE CONCOMITANT MEDICATION | DOSAGE OF THE CONCOMITANT MEDICATION | FREQ. OF THE CONCOMITANT MEDICATION | INDICATION FOR USE | EVENT ID | START DATE | STOP DATE | CONTIN-UING |
|---|---|---|---|---|---|---|---|---|
| ⌕ | ADVIL | 200MG | 3/DAY | | | | | O/R/C |
| | | 1220 | 1230 | | | | | 0/0/0 |

[DELETE SELECTED ROW] [ENTER NEW ROW]

CONMED 2

| CONCOMITANT MEDICATION | NAME OF THE CONCOMITANT MEDICATION | DOSAGE OF THE CONCOMITANT MEDICATION | FREQ. OF THE CONCOMITANT MEDICATION | INDICATION FOR USE | EVENT ID | START DATE | STOP DATE | CONTIN-UING |
|---|---|---|---|---|---|---|---|---|
| | | | | | | | | O/R/C |

[DELETE SELECTED ROW] [ENTER NEW ROW]

PAGE LEVEL QUERIES AND ANNOTATIONS

[GO BACK] [CONTINUE] [SAVE] ~1210

SECTION NAME:
EXPAND ALL
COLLAPSE ALL

▶ SECTIONS
   COMMONFORM
   DEMOGRAPHICS
   VITAL SIGNS
   AE
   CONMED
   COMMENTS
INVESTIGATOR
SIGNOFF HISTORY
SEE INSTRUCTIONS
EXIT DATA
COLLECTION EVENT

1200

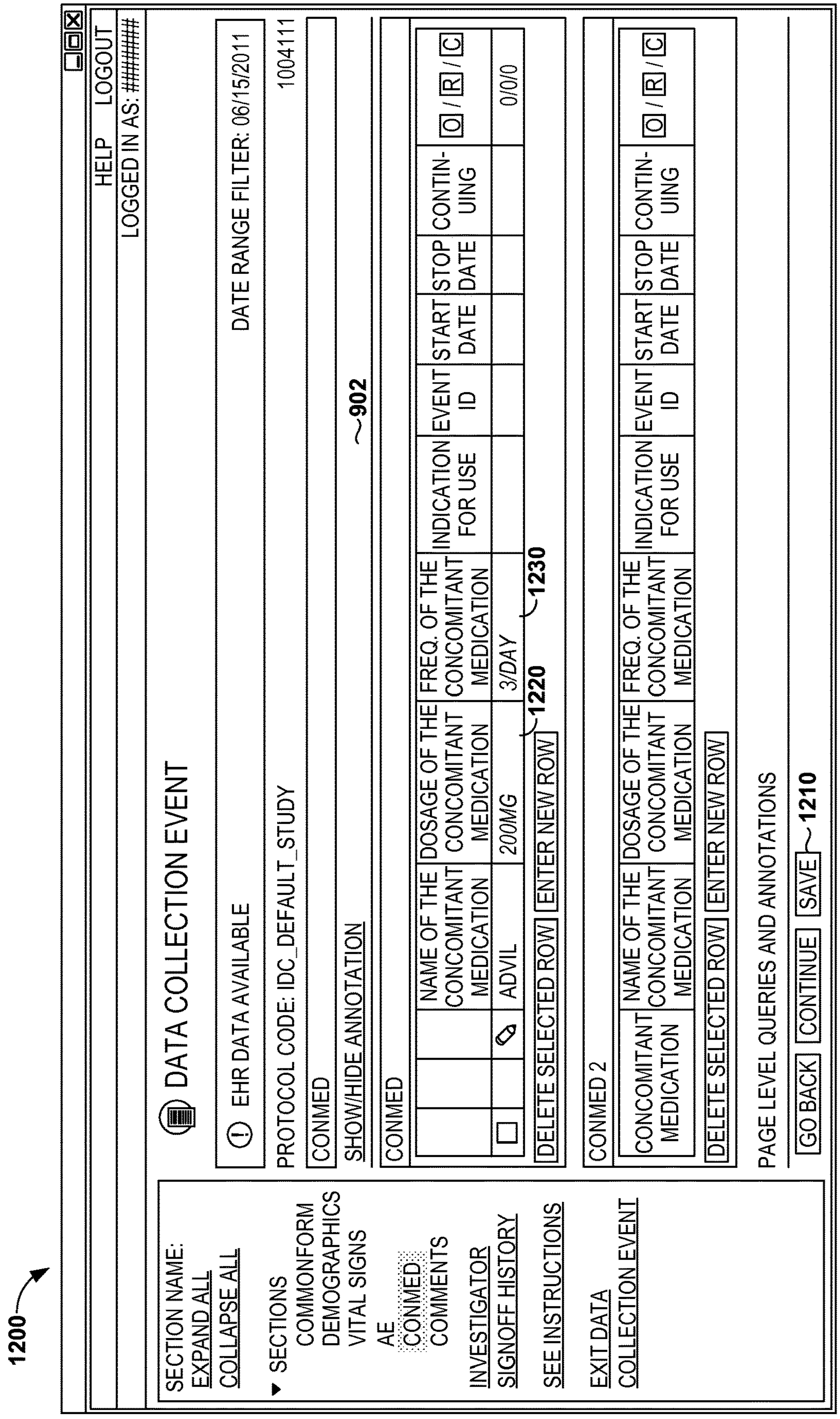

FIG. 12

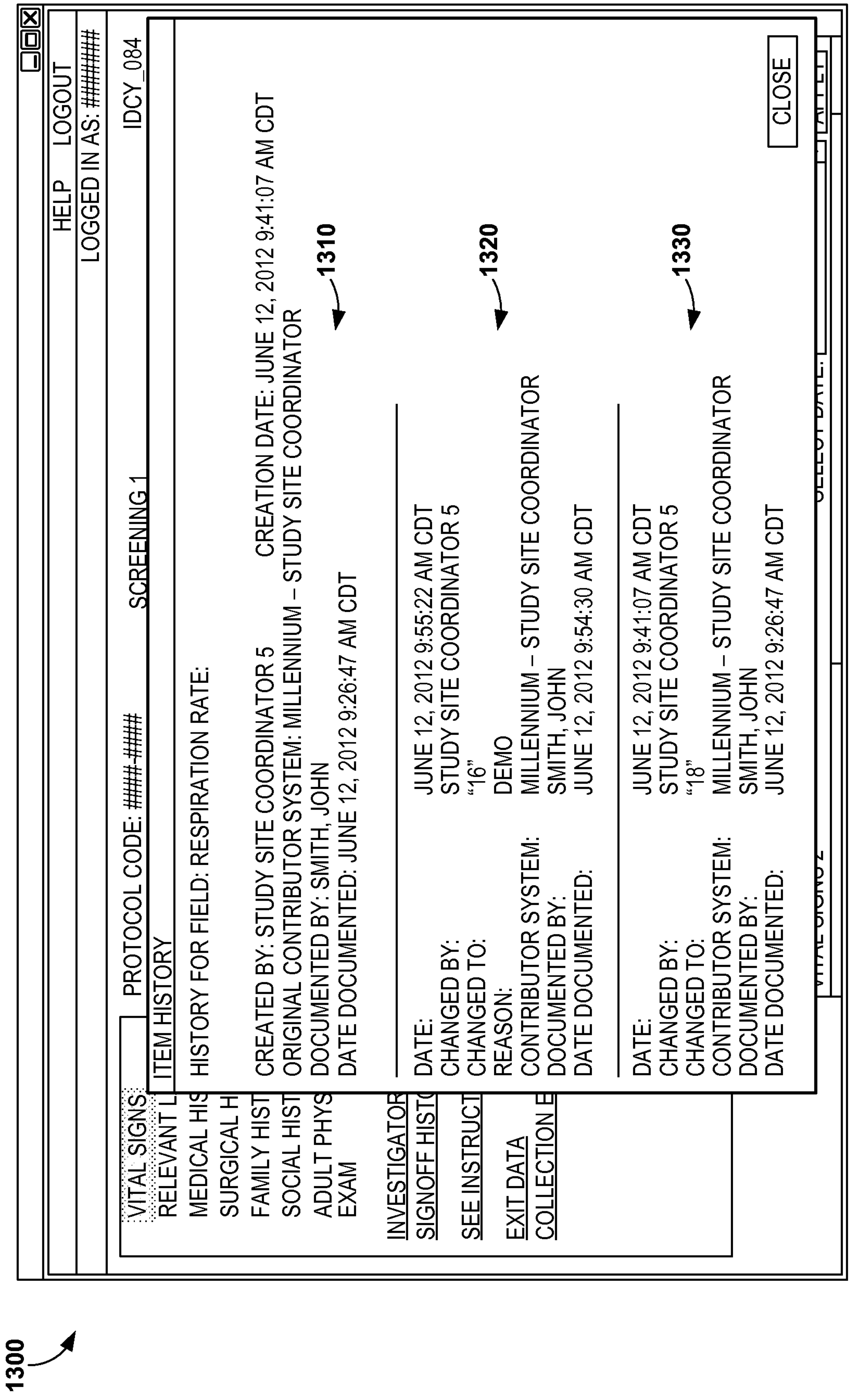

FIG. 13

PROTOCOL CODE: ####-####   SCREENING 1   IDCY_084

ITEM HISTORY

HISTORY FOR FIELD: RESPIRATION RATE:

CREATED BY: STUDY SITE COORDINATOR 5       CREATION DATE: JUNE 12, 2012 9:41:07 AM CDT
ORIGINAL CONTRIBUTOR SYSTEM: MILLENNIUM – STUDY SITE COORDINATOR
DOCUMENTED BY: SMITH, JOHN
DATE DOCUMENTED: JUNE 12, 2012 9:26:47 AM CDT                    ← 1310

DATE:                  JUNE 12, 2012 9:55:22 AM CDT
CHANGED BY:            STUDY SITE COORDINATOR 5
CHANGED TO:            "16"
REASON:                DEMO
CONTRIBUTOR SYSTEM:    MILLENNIUM – STUDY SITE COORDINATOR
DOCUMENTED BY:         SMITH, JOHN
DATE DOCUMENTED:       JUNE 12, 2012 9:54:30 AM CDT              ← 1320

DATE:                  JUNE 12, 2012 9:41:07 AM CDT
CHANGED BY:            STUDY SITE COORDINATOR 5
CHANGED TO:            "18"
CONTRIBUTOR SYSTEM:    MILLENNIUM – STUDY SITE COORDINATOR
DOCUMENTED BY:         SMITH, JOHN
DATE DOCUMENTED:       JUNE 12, 2012 9:26:47 AM CDT              ← 1330

Tabs (left side): VITAL SIGNS, RELEVANT L..., MEDICAL HIS..., SURGICAL H..., FAMILY HIST..., SOCIAL HIST..., ADULT PHYS EXAM, INVESTIGATOR SIGNOFF HIST..., SEE INSTRUCT..., EXIT DATA, COLLECTION E...

HELP   LOGOUT
LOGGED IN AS: ########

CLOSE

1300

SELECTING ALTERNATE RESULTS FOR INTEGRATED DATA CAPTURE

CROSS REFERENCE TO RELATED APPLICATIONS

This application is related to commonly assigned U.S. patent applications entitled "Filtering Values in a Closed Menu for Integrated Data Capture", "Audit Trail for Integrated Data Capture", and "Integrated Data Capture with Item Group Key", filed concurrently herewith on the same date.

BACKGROUND

In recent years, healthcare service providers have been making the transition from manual paper-based medical records to an electronic format. Commercially available computer software, such as PowerChart®, PowerChart Office®, and other Cerner Millennium® applications marketed by Cerner Corporation of Kansas City, Mo. have advanced the state of the art well beyond the conventional manual approach. Electronic-based records substantially increase the efficiency of healthcare providers and institutions. Electronic medical records (EMRs) also substantially reduce risks associated with high volumes of patient data and potential liabilities arising out of clerical errors or misinformation. The electronic format enhances communication between various providers and within institutions. As electronic clinical documentation continues to become increasingly prevalent, the variety of applications, electronic forms, electronic charts, and user interfaces, as well as the corresponding versatility of this format, continue to expand.

The data contained in EMRs is often useful to pharmaceutical or device companies, research organizations, and the like. Unfortunately, the data collection process is extremely time consuming, expensive, and often difficult. Electronic Data Capture streamlines the data collection process and increases the data accuracy for studies of drugs and medical devices.

When populating data for research, there is often more than one result collected in an electronic medical record (EMR) that applies to a particular item in a case report form. Current systems allow only one result to be electronically populated in the case report form during an integrated data capture session. If that result is not the appropriate value, some systems allow users to manually edit the value that was electronically transcribed from the EHR. Unfortunately, this may result in data discrepancies between the source documentation and the research database.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to systems, methods, and computer-readable media for, among other things, selecting alternate results for integrated data capture. In embodiments, indicators are displayed when alternate results are available for an item to be included in a case report form. In embodiments, closed menus of alternate results are presented.

Accordingly, in one embodiment, computer storage media having computer-executable instructions embodied thereon, that when executed by one or more computing devices, cause the one or more computing devices to perform a method for selecting alternate results for integrated data capture. An integrated data capture workflow is initiated from within an electronic medical record (EMR). Data is gathered from the EMR to make available to a case report form. The case report form is populated with the most recently collected values of the data. An indicator is displayed if alternate results for an item are available. A selection of the indicator is received. A closed menu of alternate results for the item is presented.

In another embodiment, a computer system that facilitates selecting alternate results for integrated data capture is provided. The computer system comprises a processor coupled to a computer storage medium, the computer storage medium having stored thereon a plurality of computer software components executable by the processor. The computer software components comprise a workflow component for initiating an integrated data capture workflow from with an EMR. A gather component gathers data from the EMR to make available to a case report form. A population component populates the case report form with the most recently collected values of the data. An indicator component displays an indicator if alternate results for an item are available. A presentation component presents a closed menu of alternate results for the item if the indicator is selected. A selection component receives a selection of an alternate result. A store component stores the case report form.

In another embodiment, computer storage media having computer-executable instructions embodied thereon that, when executed, produce a graphical user interface (GUI) to facilitate selecting alternate results for integrated data capture. A workflow display area is configured to display an integrated data capture workflow. An indicator display area is configured to display an indicator if alternate results for an item are available. An alternate results display are is configured to display a closed menu of alternate results for the item when the indicator is selected.

BRIEF DESCRIPTION OF THE DRAWINGS

The present invention is described in detail below with reference to the attached drawings figures, wherein:

FIGS. 7-15 are illustrative screen displays illustrating various integrated data capture, in accordance with embodiments of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention empower a clinician's or organization's ability to harness pertinent research data. Embodiments present advantages over other systems which are limited to loading single instances of data into memory. Embodiments present advantages over other systems which lack filtering capabilities. Embodiments present advantages over other systems which do not include audit information for both the source data and the case report form. Embodiments present advantages over other systems which lack the ability to maintain congruity between various items of data.

Figure 1:
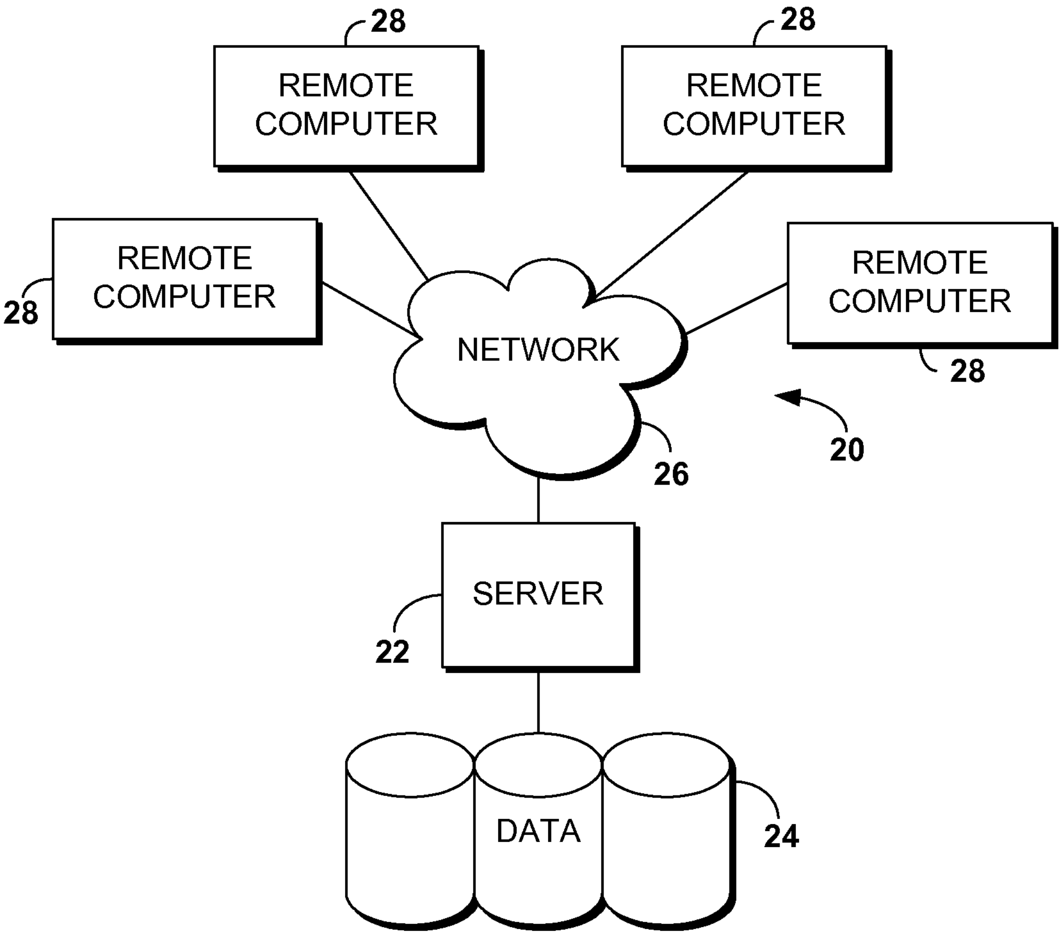
FIG. 1 is a block diagram of an exemplary computing system suitable for use in implementing embodiments of the present invention.

Having briefly described embodiments of the present invention, an exemplary operating environment suitable for use in implementing embodiments of the present invention is described below. Referring to FIG. 1 an exemplary computing environment with which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary computing environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22.

Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22. The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnections are well known. Accordingly, additional details concerning the internal construction of the server 22 and the remote computers 28 are not further disclosed herein.

Figure 2:
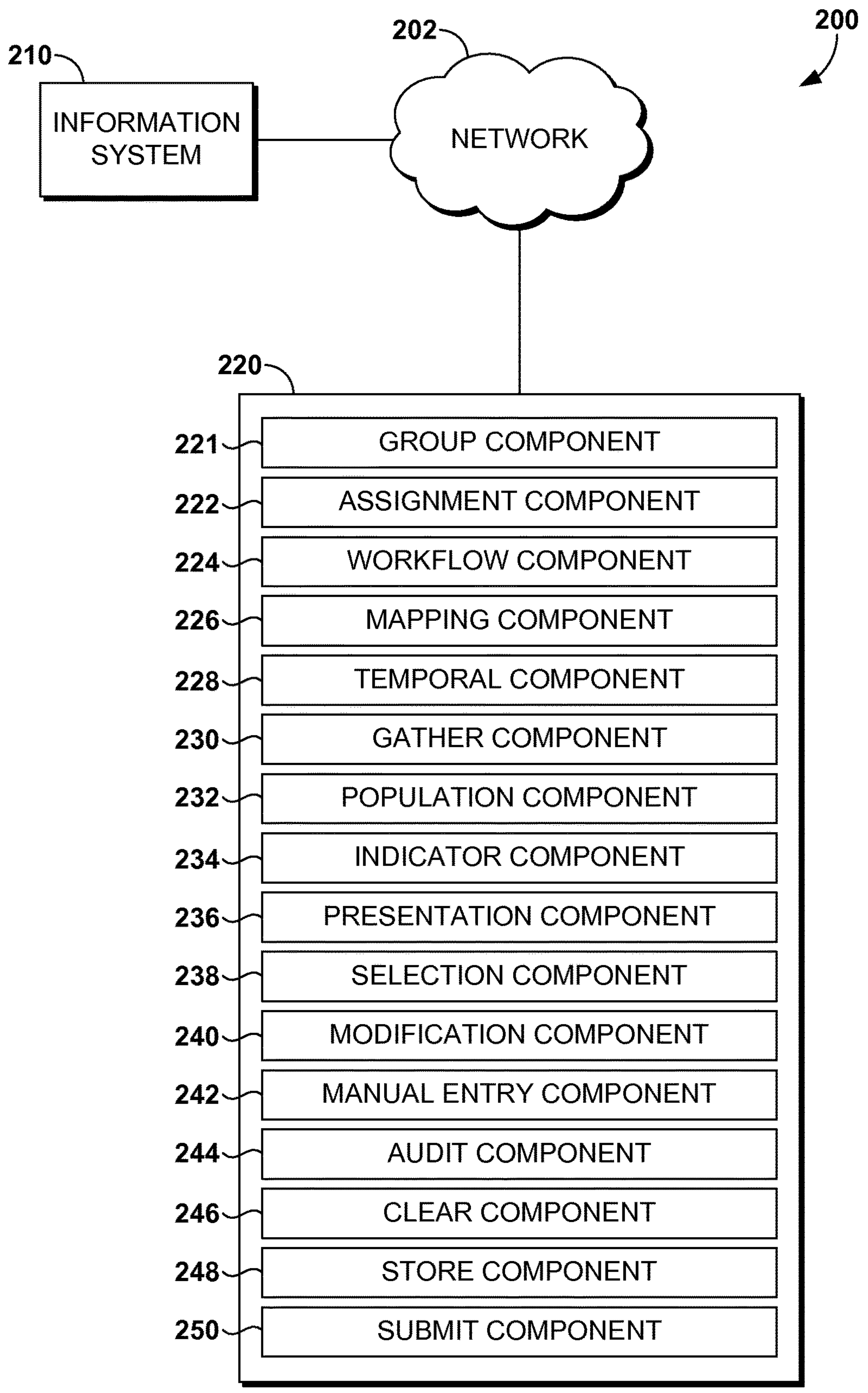
FIG. 2 schematically shows a network environment suitable for performing embodiments of the invention.

Referring now to FIG. 2, a block diagram is provided illustrating an exemplary system 200 in which a integrated data capture engine 220 is shown interfaced with an information system 210 in accordance with an embodiment of the present invention. The information system 210 may be a comprehensive computing system within a clinical environment similar to the exemplary computing system 20 discussed above with reference to FIG. 1.

The information system 210 may be connected via the network 202 to one or more databases, storing EMRs associated with patients or research data collected by pharmaceutical or device companies, research organizations, and the like. The databases may also store case report forms created by integrated data capture system 220. An internal database may be utilized by information system 210 and may be stored within the information system 210 or external to the information system 210. Each of the pharmaceutical or device companies, research organizations, and the like, subscribing to integrated data capture engine 220 may similarly be connected via the network 202 to the one or more databases, the information system 210, or the integrated data capture engine 220.

The integrated data capture engine 220 is generally configured to facilitate gathering data from an EMR and creating case report forms, reducing the error, work effort, and time required often associated with the integrated data capture process. Each case report form created by integrated data capture engine 220 is populated with select data from the EMR. The ability to maintain congruity across data sources, in various embodiments, is enhanced by providing alternate results for the select data in a closed menu.

As shown in FIG. 2, the integrated data capture engine 220, in various embodiments, includes group component 221, assignment component 222, workflow component 224, mapping component 226, temporal component 228, gather component 230, population component 232, indicator component 234, presentation component 236, selection component 238, modification component 240, manual entry component 242, audit component 244, clear component 246, store component 248, and submit component 250.

In an embodiment, group component 221 receives a selection of a group of items from the EMR. This allows a group of items that may be related to be associated such that the group of items will be populated into the case report form together. Such grouping maintains congruity between the items of data belonging to the group. For example, an EMR may contain data entries for a particular group of items every 15 minutes. By grouping the items together, a user ensures that the entry populated into the case report form for each of the items in the group is taken from the entry at the same or substantially the same time as recorded in the EMR. Similarly, an EMR may contain a medication name and dosage as two discrete fields. However, the results that were signed together in the EMR must remained joined in the case report form for accuracy. Such functionality prevents mix and match results from different fields in the EMR.

In one embodiment, group component 221 ensures each item of the group of items is populated into the case report form in the same order and grouping in which they were recorded in the EMR. In one embodiment, group component 221 further allows a user to pick between groups of results available in the EMR to be populated into a single set of desired fields on a case report form. In one embodiment, group component 221 provides a visual indication that there are multiple groups of results available to be populated into a group of items on a case report form.

In an embodiment, assignment component 222 assigns an item group key to at least one item of the group of items. The item group key allows a subset of fields to be indicative of the uniqueness of a specific set of values. For example, though the medication name, dosage, and date administered are all collected together in the EMR, the creator of the case report form might wish to enable the user to pick the relevant date among the different dates a particular drug was administered. In this example, the "medication name" and "dosage" fields would indicate the uniqueness to the group as a whole, while "date administered" can be selected by the user to appropriately populate the case report form with data associated with the selected date administered.

In an embodiment, workflow component 224 initiates an integrated data capture workflow from within an EMR. The integrated data capture workflow guides a user through the steps necessary to create and populate a case report form. In one embodiment, workflow component 224 provides a graphical user interface (GUI) that guides the user through selecting, designating, and selecting alternate results for the desired data. In another embodiment, workflow component 224 provides textual instructions to facilitate the integrated data capture process. In yet another embodiment, workflow component 224 provides an interactive menu to facilitate the integrated data capture process. In another embodiment, workflow component 224 provides a combination of a GUI, textual instructions, and an interactive menu to facilitate the integrated data capture process.

In an embodiment, mapping component 226 maps the EMR to the case report form. This allows a user to visually select data associated with the EMR and place in a desired location associated with the case report form. In one embodiment, mapping component 226 allows a user to define a protocol or mapping such that additional case report forms can be created using the same protocol. In one embodiment, mapping component 226 allows a user to give context to the particular protocol. In another embodiment, mapping component 226 works with gather component 230 to gather alternate results in addition to the most recently collected data and maintains these items in temporary memory until selection component 238 receives a selection of the desired instance of data.

In an embodiment, temporal component 228 receives a time range associated with data from the EMR. This allows a user populating a case report form to limit data gathered by gather component 230 to a particular time range within the EMR. For example, if an interest in data associated with a particular event or treatment is desired, a user can restrict data gathered by gather component to a time range associated with the particular event or treatment.

In an embodiment, gather component 230 gathers data from the EMR to make available to a case report form. In one embodiment, gather component 230 gathers data in response to a selection made by a user. In one embodiment, gather component 230 gathers the most recently collected values of the data. In one embodiment, gather component 230 gathers multiple results associated with the data that may be presented to a user as alternate results for an item of data. In one embodiment, gather component 230 gathers data associated with a particular time ranged received by temporal component 228.

In an embodiment, population component 232 populates the case report form with the most recently collected values of the data that has been gathered by gather component 230. In one embodiment, population component 232 temporarily populates the case report form with the most recently collected values of the data until alternate results are selected for a particular item of data. If alternate results are selected, population component 232 populates the case report form with the alternate results. In one embodiment, population component 232 maintains the most recently collected values of data and any associated alternate results gathered by gather component 230 in memory and does not populate the case report form until a user selects the most recently collected value or an alternate result for each particular item of data.

In an embodiment, indicator component 234 displays an indicator that an alternate result for an item is available. This allows a user to determine whether to allow the case report form to be populated with the most recently collected value for that item or the most recently collected value for a selected time range for that item or to select an alternate result for that particular item.

In an embodiment, presentation component 236 presents a closed menu of alternate results for the item if the indicator is selected. The closed menu provides a user with selectable alternatives for a particular item of data and prevents a user from manually entering a result for a particular item of data. As can be appreciated, the closed menu greatly reduces or prevents errors in the case report form. In one embodiment, presentation component 236 presents values associated with the data for the time range received by the temporal component in a closed menu.

In an embodiment, selection component 238 receives a selection of a result. In an embodiment, the result is an alternate result. The selection of an alternate result is received from a list of alternate results provided in a closed menu by presentation component 236. Selection component 238 only allows a user to select an alternate result from the closed menu. As noted above, this greatly reduces or prevents errors in the case report form that are often the result of manual editing.

In an embodiment, modification component 240 modifies data associated with the item group key to maintain congruity between the data populated in the case report form for the group of items. For example, if a case report form has already been populated with data and a user desires to select an alternate result for the item group key, modification component 240 automatically modifies the items associated with the item group key to maintain congruity between the data associated with the items in the group.

In an embodiment, manual entry component 242 does not allow manual editing for a particular item of data. In another embodiment, manual entry component 242 only allows manual editing for contextual information associated with a particular item of data, but not the data itself. This allows a clinician to document information that may provide insight into or explanation for a particular result without actually modifying the result.

In an embodiment, audit component 244 adds an audit trail to the case report form. In embodiments, the audit trail includes an identification of the source system, the documenting clinician, the date and time of entry into the EMR, a creation date, a creation author, or a combination thereof. The creation date and creation author represent the date and author associated with creating the case report form, as opposed to the documentation date and documenting clinician for the data's original entry into the EMR. In one embodiment, audit component includes alternate result audit information. In embodiments, alternate result audit information includes a change date for an alternate result, a change author for the alternate result, a change source system for the alternate result, a documenting clinician for the alternate result, a documenting date (the date and time of entry into the EMR) for the alternate result, or any combination thereof. In one embodiment, a change reason is included in the alternate result audit information only if an alternate result is replacing any portion of data already saved in the case report form.

In an embodiment, clear component 246 receives a selection to clear unwanted data from the case report form. This may be particularly useful if various items of data are populated in the case report form as a group. In some instances, a particular item of data may be misleading, inaccurate, or not desired. For example, a medication, condition, or other event may have skewed the result for a particular item of data. Rather than leaving that particular item of data in the case report form, a user may desire to clear that item of data.

In an embodiment, store component 248 stores the populated case report form. In one embodiment, store component 248 stores the case report form in a database associated with the integrated data capture engine 220. In another embodiment, store component 248 stores the case report form in an external database that integrated data capture engine 220 communicates with via the network 202. In another embodiment, store component 248 stores the case report form in a database associated with information system 210.

In an embodiment, submit component 250 submits the case report form. This allows the case report form to be communicated from its place of storage to a pharmaceutical or device company, research organization, and the like that has subscribed to or has a particular interest in that case report form.

Figure 3:
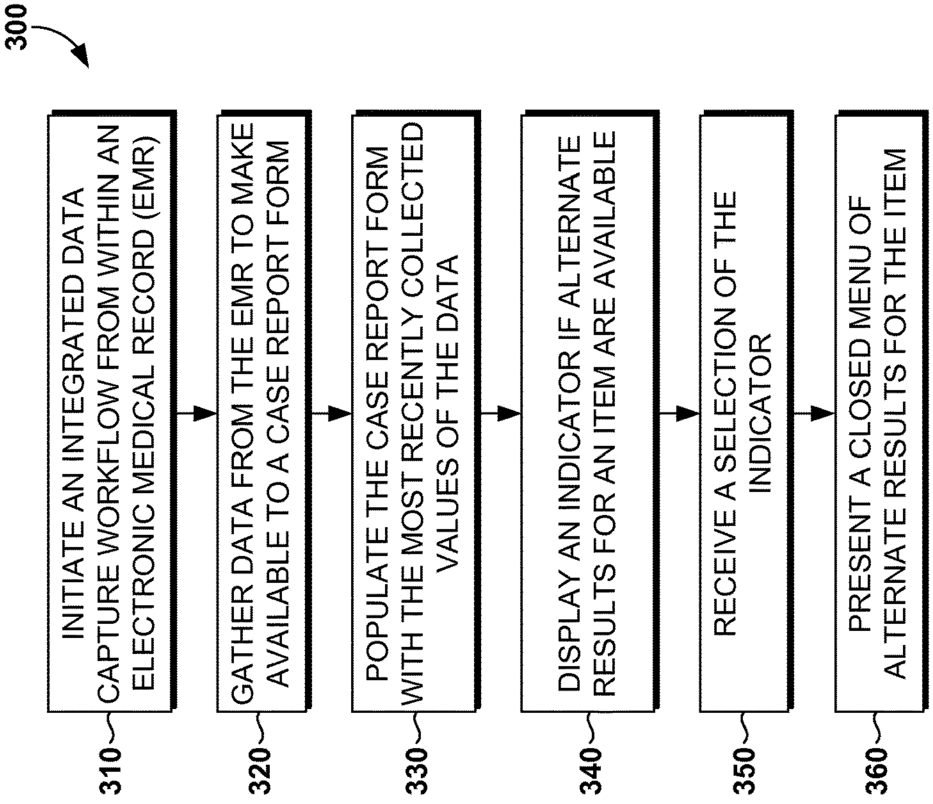
FIG. 3 is a flow diagram showing a method for selecting alternate results for integrated data capture, in accordance with an embodiment of the present invention.

With reference to FIG. 3, an exemplary flow diagram representative of a method for selecting alternate results for integrated data capture, in accordance with an embodiment of the present invention is shown and referenced generally by numeral 300. Method 300 may be implemented using the above-described exemplary computing system environment (FIG. 1). Initially, as shown at step 310, an integrated data capture workflow is initiated from within an EMR. Data is gathered from the EMR, at step 320, to make available to a case report form. At step 330, the case report form is populated with the most recently collected values of the data. In one embodiment, rather than populating the case report form with the most recently collected values of the data, the data gathered from the EMR including any alternate results is loaded into memory until a user selects whether to include the most recently collected value or an alternate result in the case report form. An indicator is displayed if alternate results are available for an item at step 340. At step 350, a closed menu of alternate results is presented for the item.

In one embodiment, a selection of an alternate result is received. The case report form is updated with the alternate result. In one embodiment, a name of a person who documented the result in the EMR and a date and time associated with the result is populated into the case report form in association with the alternate result. In one embodiment, an audit trail is received for the case report form. This allows a user to determine audit information related to changes made to the case report form.

In one embodiment, manual updates for the data are not allowed. This ensures the accuracy of data being populated into the case report form from the EMR. In one embodiment, manual entry of contextual information is received. The contextual information may provide insight into a particular result populated into the case report form, without allowing any editing of the result itself. In one embodiment, a selection to clear unwanted data for the case report form is received.

In one embodiment, the case report form is created utilizing the mapping. The mapping allows a user to define or use a particular protocol such that additional case report forms can be created utilizing the same protocol or mapping. In addition, the mapping provides context to the particular protocol.

In one embodiment, a selection of a date range is received. The date range specifies that a user is interested in results in selecting from results in that particular date range for inclusion in the case report form.

In one embodiment, the case report form is stored in a database. In one embodiment, the database is associated with the integrated data capture engine (220 in FIG. 2). In another embodiment, the database is associated with the information system (210 in FIG. 2). In another embodiment, the database is external to both the integrated data capture engine and the information system. In one embodiment, the case report form is submitted to a pharmaceutical or device company, research organization, or the like.

Figure 4:
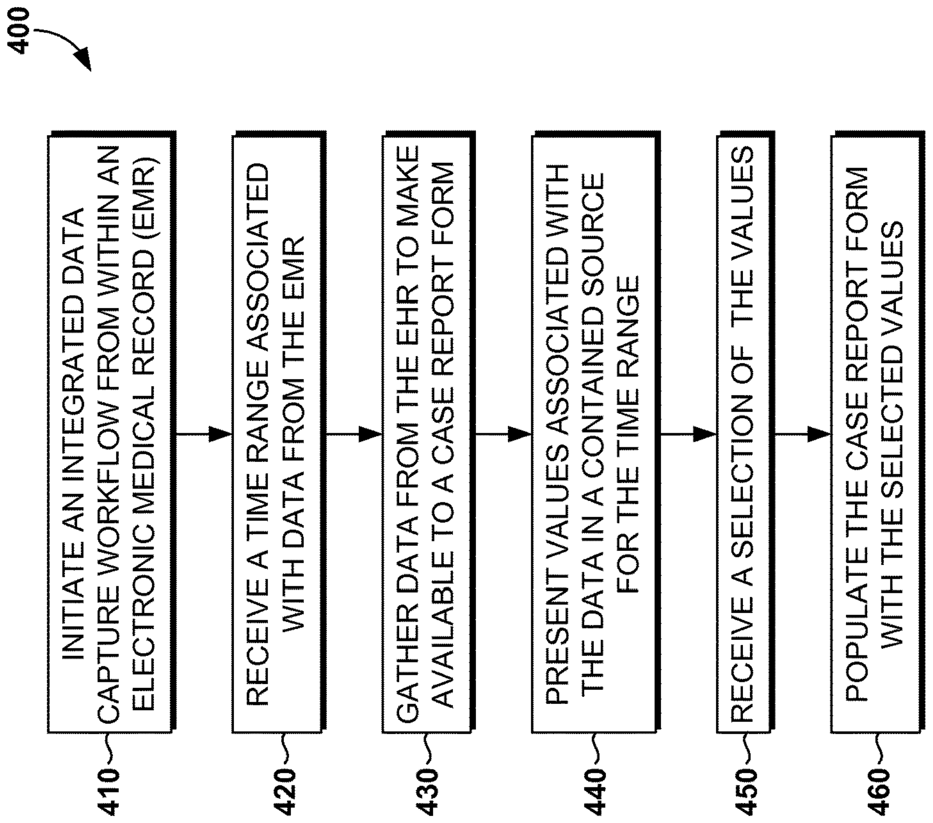
FIG. 4 is a flow diagram showing a method for facilitating filtering values in a closed menu for integrated data capture, in accordance with an embodiment of the present invention.

With reference to FIG. 4, an exemplary flow diagram representative of a method for facilitating filtering values in a closed menu for integrated data capture, in accordance with an embodiment of the present invention is shown and referenced generally by numeral 400. Method 400 may be implemented using the above-described exemplary computing system environment (FIG. 1). Initially, as shown at step 410, an integrated data capture workflow is initiated from within an EMR. A time range associated with data from the EMR is received at step 420. Data is gathered, at step 430, from the EMR to make available to a case report form. Values associated with the data are presented in a closed menu for the time range at step 440. At step 450, a selection of the values is received. The case report form is populated with the selected values at step 460.

In one embodiment, an indicator is displayed if an alternate result is available for an item. For example, if one of the items of data has multiple values of data that are gathered from the EMR, an indicator is displayed. In one embodiment, a selection of the indicator is received. The selection of the indicator, in one embodiment, causes a menu of alternate results to be presented for the item. In one embodiment, a selection of an alternate result is received. In one embodiment, an audit trail is displayed for the selection of values.

In one embodiment, manual updates to the values are not allowed. In one embodiment, manual entry of contextual information for a value is received. In one embodiment, an unwanted value is cleared when an indication to clear the unwanted value is received. For example, a user may determine that the particular result is not relevant or inaccurate due to the subject of the result undergoing a treatment or having a condition at the time the result was recorded. Rather than allowing the user to modify or manually edit the result, the user can clear the unwanted value.

In one embodiment, the case report form is stored, such as in a database. In one embodiment, the case report form is submitted to a research record. In one embodiment, the case report form is submitted to a pharmaceutical or device company, a research organization, or the like.

Figure 5:
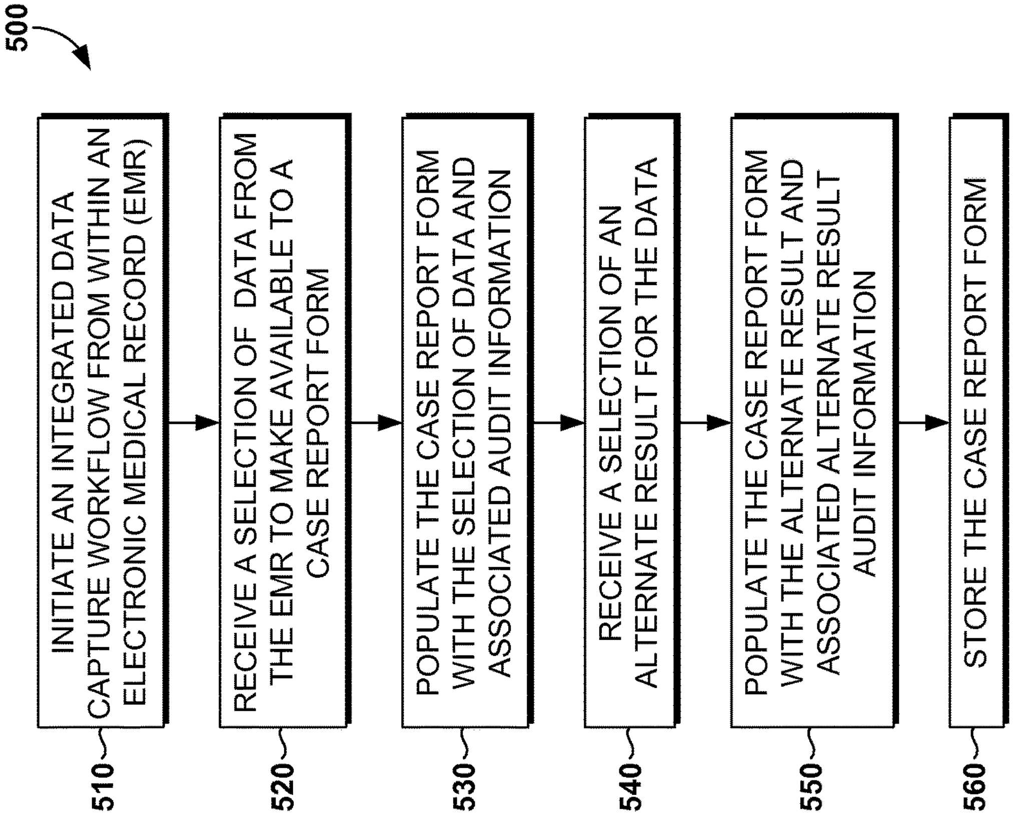
FIG. 5 is a flow diagram showing a method for facilitating an audit trail for integrated data capture, in accordance with an embodiment of the present invention.

With reference to FIG. 5, an exemplary flow diagram representative of a method for facilitating an audit trail for integrated data capture, in accordance with an embodiment of the present invention is shown and referenced generally by numeral 500. Method 500 may be implemented using the above-described exemplary computing system environment (FIG. 1). Initially, as shown at step 510, an integrated data capture workflow is initiated from within an EMR. At step 520, a selection of data from the EMR to make available to a case report form is received. The case report form is populated, at step 530, with the selection of data and associated audit information. In one embodiment, the audit information includes a source system. The source system identifies the source of the data. In one embodiment, the audit information includes the documenting clinician. The documenting clinician identifies the clinician who documented the data in the EMR. In one embodiment, the audit information includes the data and time of entry into the EMR. In one embodiment, the audit information includes a creation date. The creation date identifies the date and/or time the data was populated from the EMR into the case report form. In one embodiment, the audit information includes a creation author. The creation author identifies the clinician who initiated the integrated data capture workflow to create the case report form.

At step 540, a selection of an alternate result for the data is received. The case report form is populated, at step 550, with the alternate result and associated alternate result audit information. In one embodiment, alternate result audit information includes a change date for the alternate result. The change date identifies the date the result was changed to the alternate result within the case report form. In one embodiment, the alternate result audit information includes a change author for the alternate result. The change author identifies the clinician who selected the alternate result. In one embodiment, the alternate result audit information includes a change reason for the alternate result. The change reason provides context describing the reason the alternate result was selected. In one embodiment, a change reason is included in the alternate result audit information only if an alternate result is replacing any portion of data already saved in the case report form. In one embodiment, the alternate result audit information includes a source system for the alternate result. The source system identifies the source system of the alternate result. In one embodiment, the alternate result audit information includes a documenting clinician for the alternate result. In one embodiment, the alternate result audit information includes a date and time of entry into the EMR for the alternate result. The case report form is stored at step 560.

Figure 6:
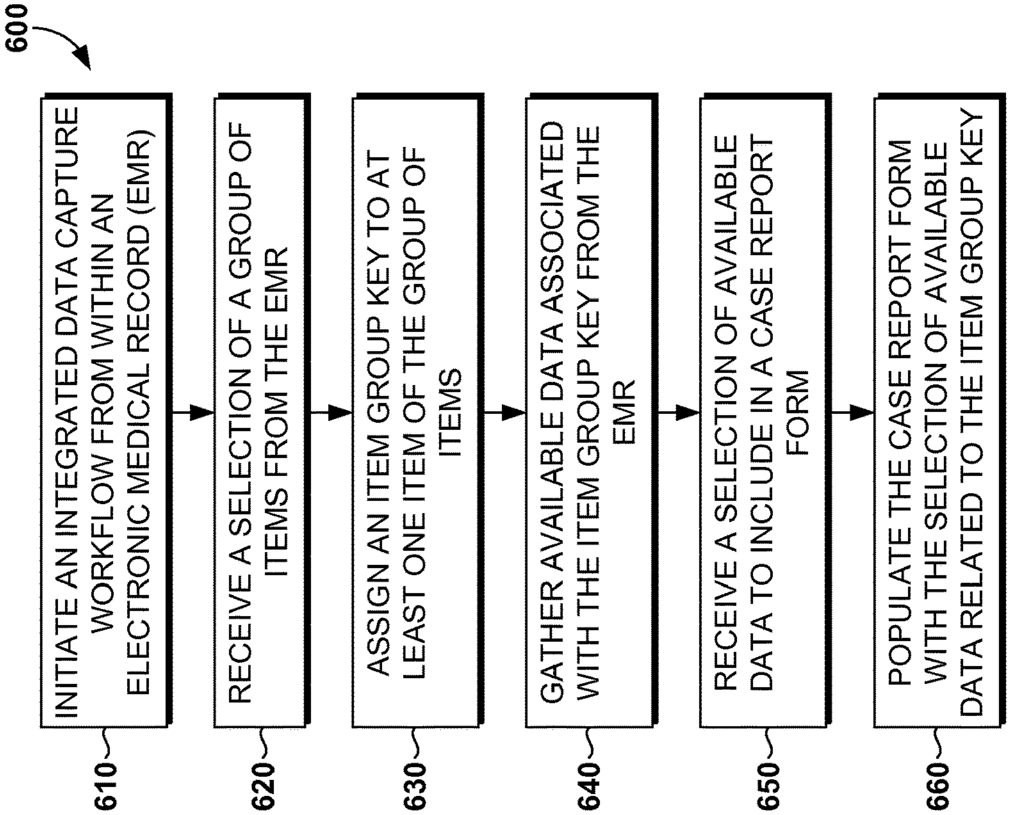
FIG. 6 is a flow diagram showing a method for facilitating integrated data capture with an item group key, in accordance with an embodiment of the present invention.

With reference to FIG. 6, an exemplary flow diagram representative of a method for facilitating integrated data capture with an item group key, in accordance with an embodiment of the present invention is shown and referenced generally by numeral 600. Method 600 may be implemented using the above-described exemplary computing system environment (FIG. 1). Initially, as shown at step 610, an integrated data capture workflow is initiated from within an EMR. A selection of a group of items from the EMR is received at step 620. The group of items represents data that should be populated as a group from the EMR into the case report form. Grouping the items ensures that the data is moved as a group to maintain congruity between the data. For example, a user may determine that certain items representing measurements associated with a patient (e.g., blood pressure, heart rate, medication, dosage, etc.) are relevant to a case report form. As can be appreciated, it is important for each of those values to be taken from the EMR in the same time frame. Accordingly, the user groups those items together so that when the case report form is populated, each value for the group is populated with the same, or substantially the same, date and time stamp. This allows the data to be more meaningful because a measurement of blood pressure and heart rate can be associated with particular dosage of medication at a particular time according to the values charted in the EMR.

An item group key is assigned, at step 630, to at least one item of the group of items. At step 640, available data associated with the item group key is gathered from the EMR. In one embodiment, a visual indication is provided that multiple instances of available data are available for the item group key. For example, continuing the example from above, medication may be selected as the item group key. If a patient's EMR indicates the patient has received the medication in variations of doses, then a visual indication is provided that data associated with the medication is available for different doses. In one embodiment, the available data is presented to a user as alternate results associated with the item group key. Rather than just populating the case report form with the most recently collected data for that medication, the alternate results allows the user to select data associated with the medication for the dose the user is interested in for that particular case report form. In one embodiment, the alternate results are presented in a closed menu. In one embodiment, a temporal filter is received for the item group key. In one embodiment, the closed menu of alternate results is responsive to the temporal filter. This allows a user to select a desired time frame for gathering the data associated with the item group key from the EMR.

A selection of available data to include in a case report form is received at step 650. In one embodiment, the selection of the alternate result for each of the group of items includes receiving a name of a person who documented the result in the EMR and a date and time associated with the result. The case report form is populated, at step 660, with the selection of available data and the item group key. In one embodiment, manual entry of contextual information is received for the selection of available data. In one embodiment, manual entry of contextual key information is received for the item group key. The contextual information allows the user to provide context for a particular item of data or the item group key, such as indicating why the data may be abnormal, inaccurate, etc. without allowing the user to manually edit the data received from the EMR.

In one embodiment, a modification of data associated with an item within the case report form. For example, a user may determine that a particular item of data that has been populated into the case report form is not the desired item of data. The user may determine that a different item of data should be populated in its place. Accordingly, the user modifies that item with another item of data. In one embodiment, an audit trail is received for the modification. The audit trail contains at least part of the audit information or alternate result audit information described above. In one embodiment, modifying an item of data that is part of a group causes other items associated with the group to be modified in accordance with the modification of data. For example, if data corresponding to a different dose or time is desired, a user may select data corresponding to the desired dose or time. Because that particular item of data is associated with a group, all data associated with the group is modified to the newly selected dose or time. This allows the case report form to maintain congruity for the data associated with that group. As can be appreciated, dose and time are merely used as an example and any item of data associated with a group can be modified, thereby modifying data associated with the group as a whole.

Figure 7:
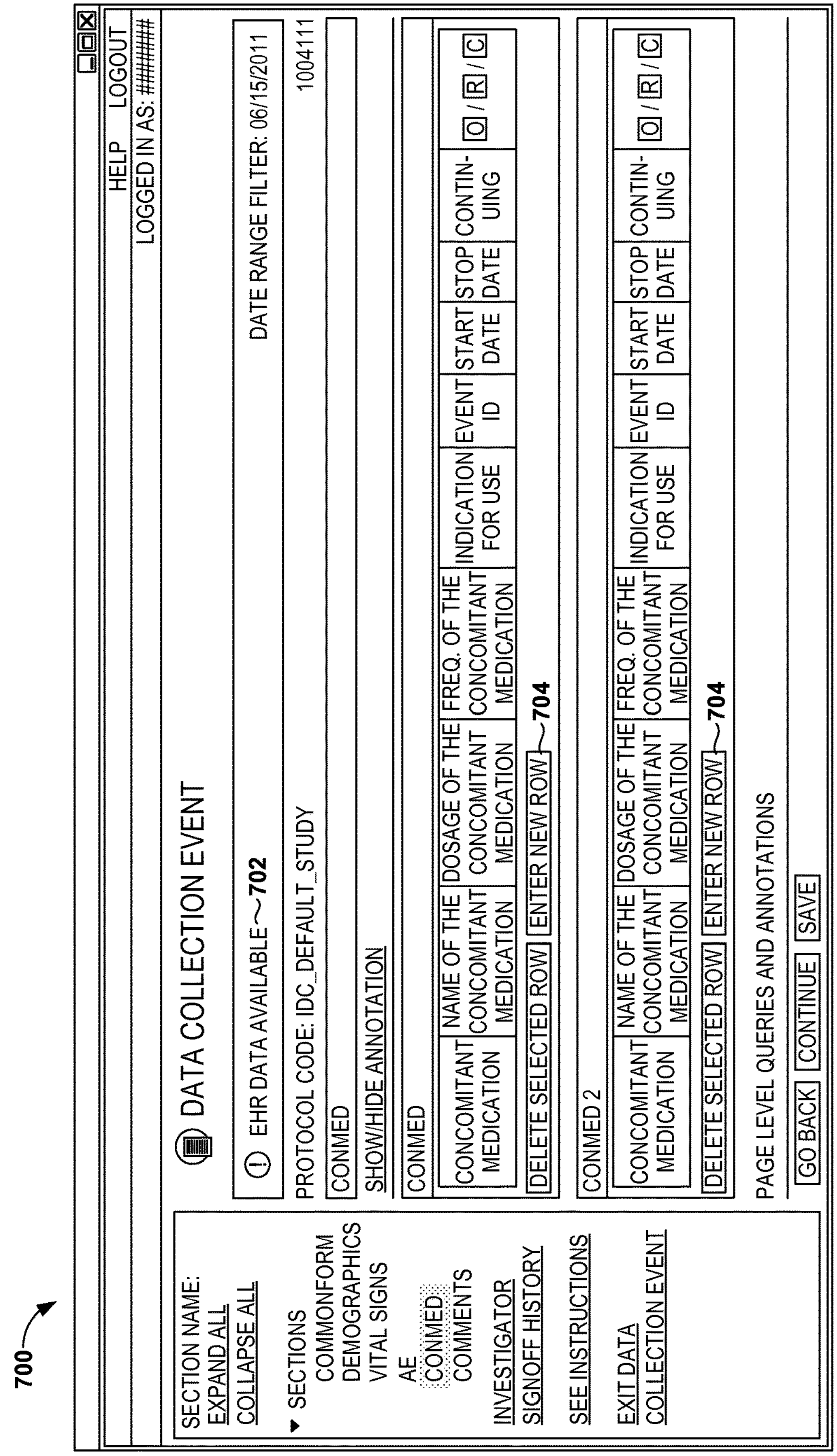
Figure 8:
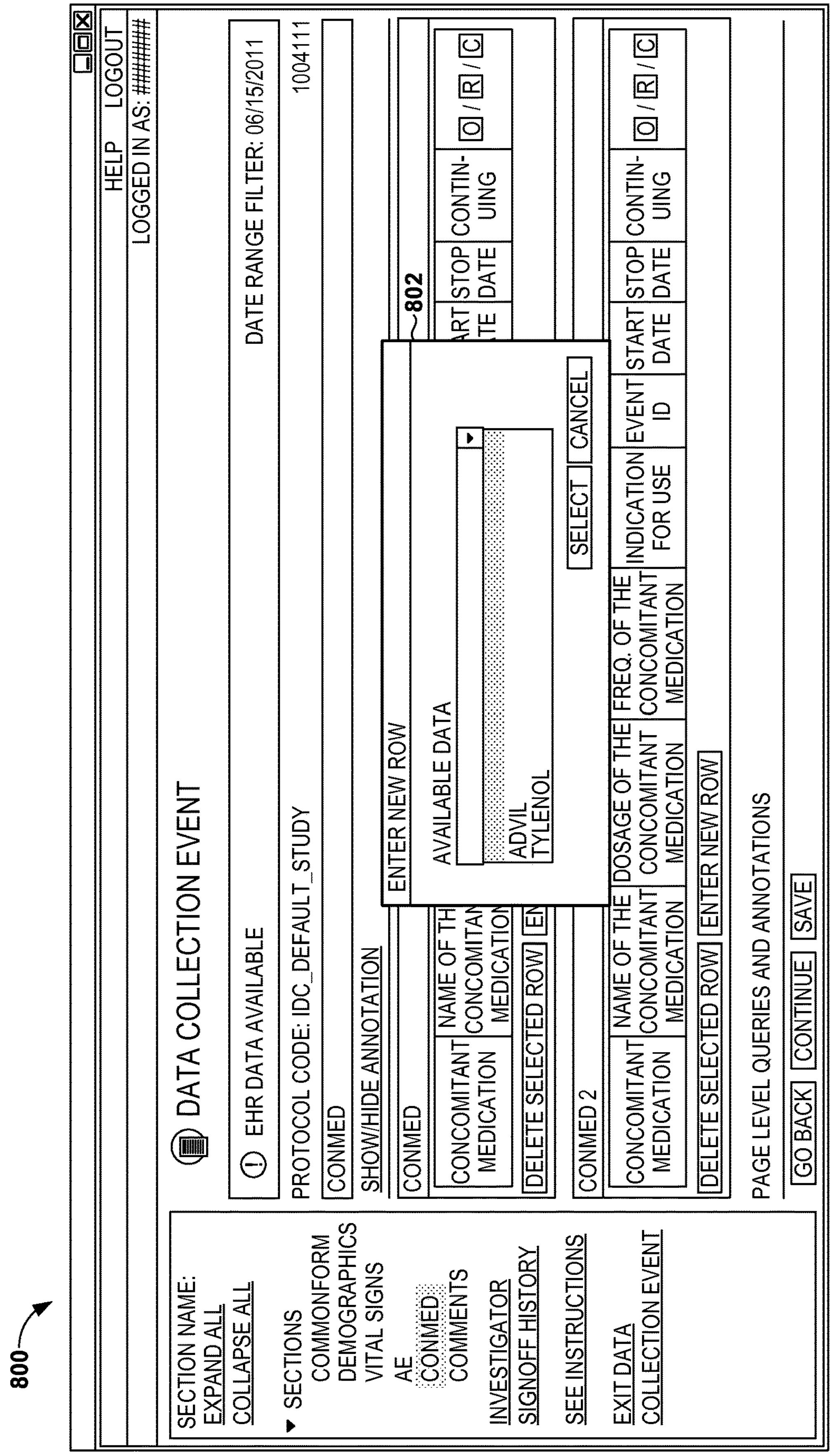
Figure 9:
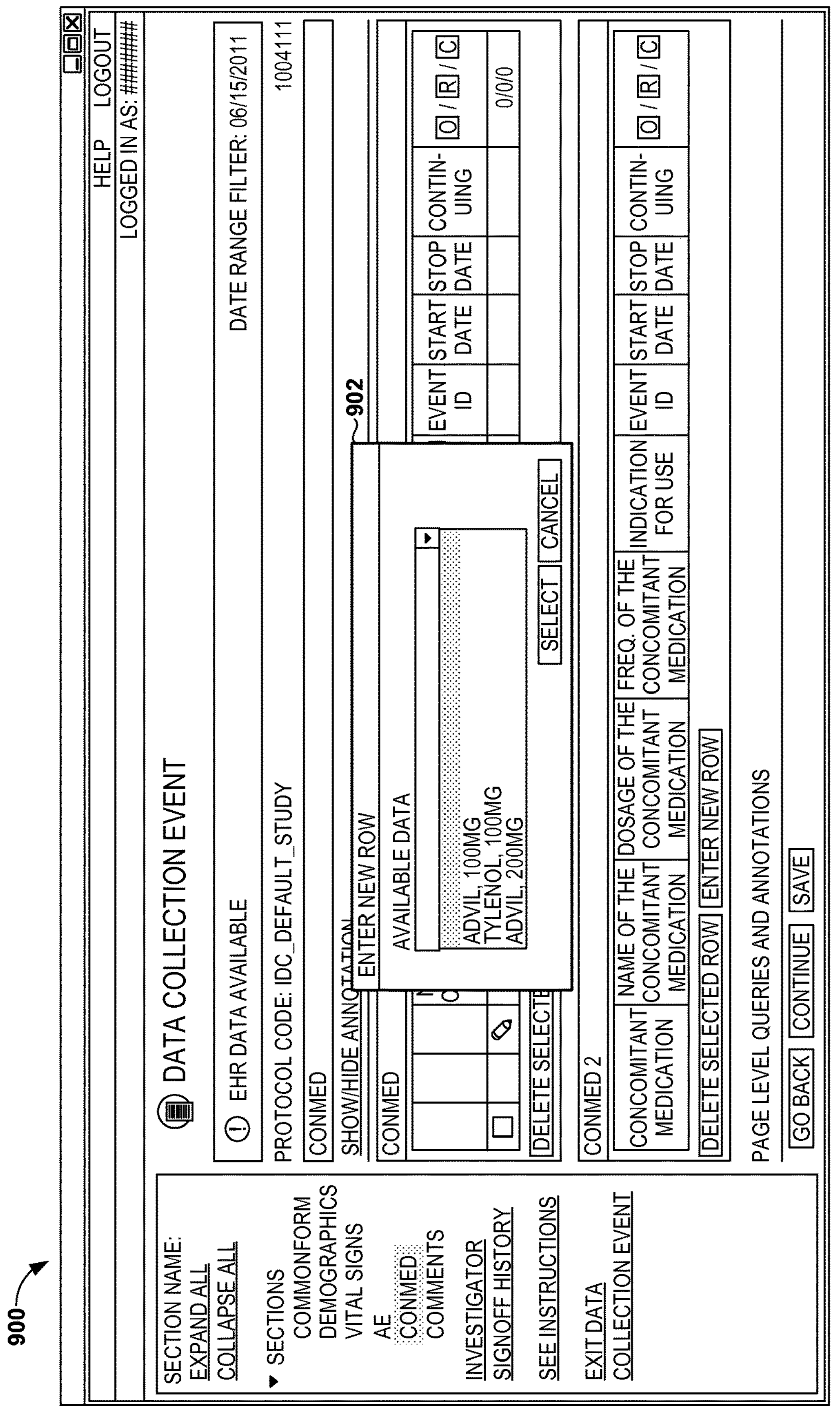
Figure 10:
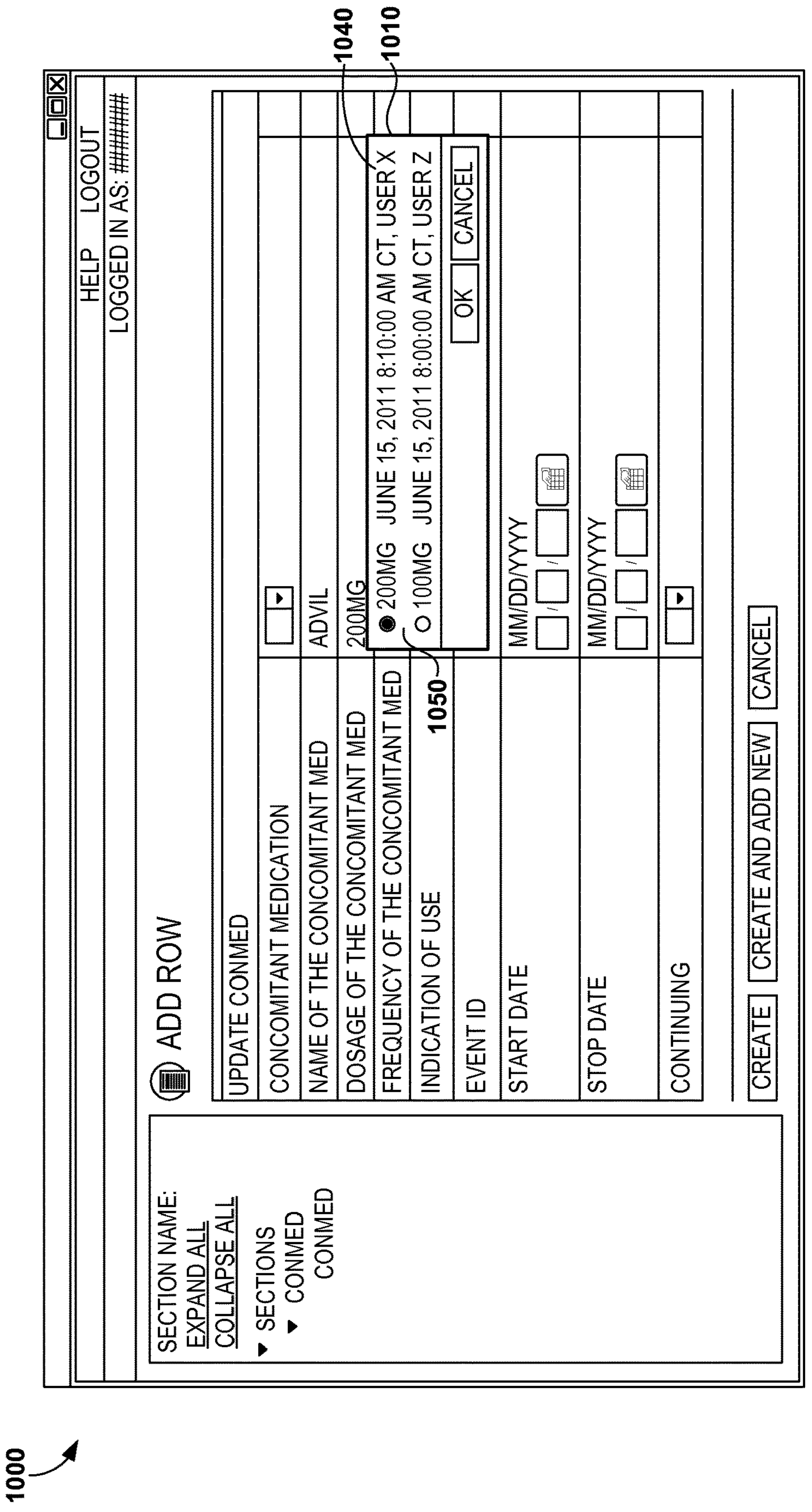
Figure 11:
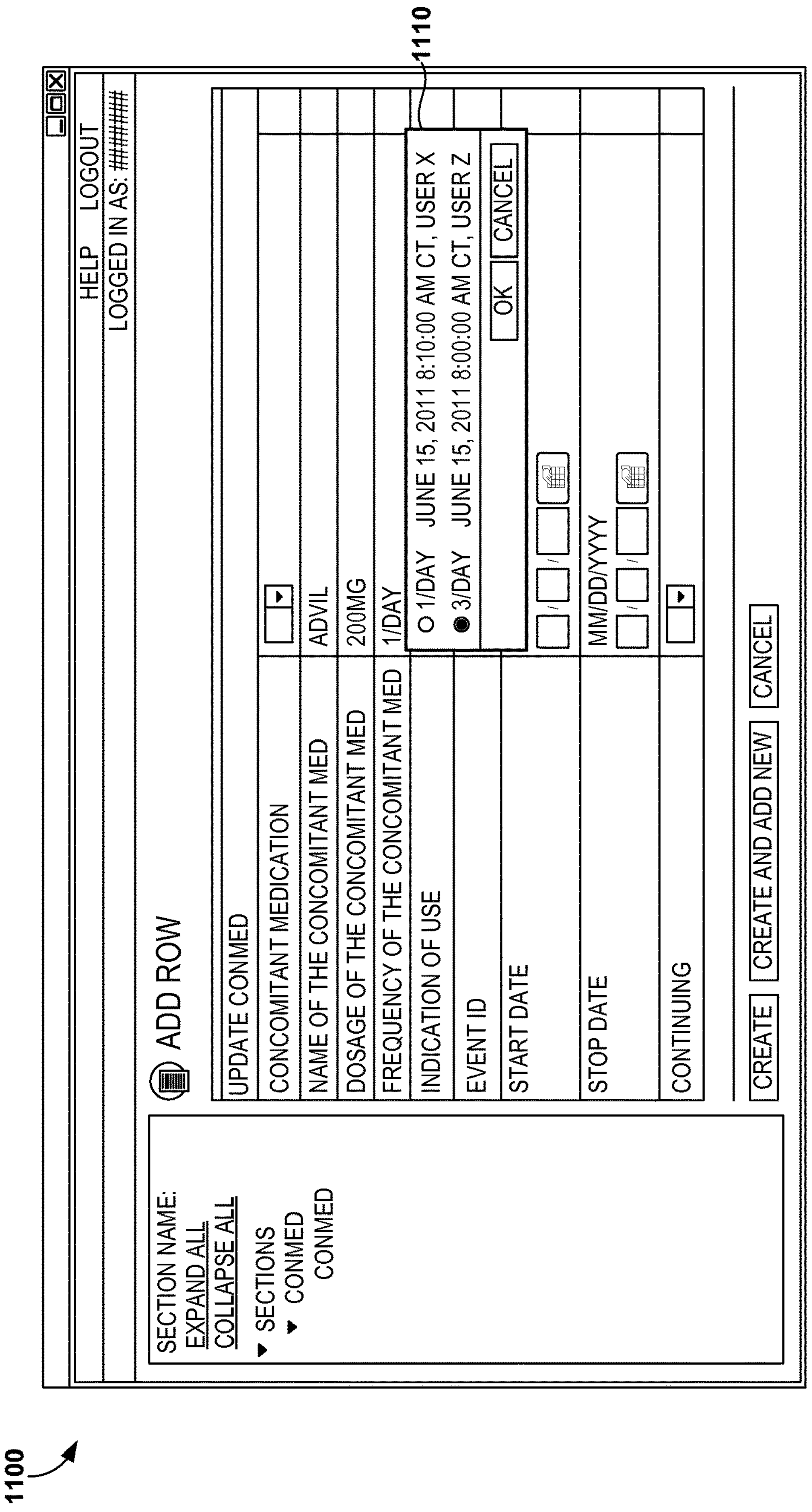

Referring now to FIGS. 7-14, illustrative screen displays 700, 800, 900, 1000, 1100, 1200, and 1400, illustrate integrated data capture, in accordance with embodiments of the present invention. Referring now to FIG. 7, an integrated data capture workflow display area includes a data indicator 702 indicating that data is available from the EMR. A user can add rows to the case report form by selecting one of the new row buttons 704. After selecting one of the new row buttons, and referring now to FIG. 8, available data is presented to the user for selection as an item group key in the item group key display area 802. In this example, the item group key is medication. Referring now to FIG. 9, the item group key display area 902 lists both medication and dose as item group keys.

Once a user has selected the desired item group key, an alternate results display area 1010 displays a closed menu of alternate results for the item. A source audit display area 1040 displays audit information associated with the data from a source system. The data includes the date and time the data was documented in the source system as well as the name of the documenting clinician. A values display area 1050 displays the values associated with the data in a closed menu. If other items of the group include alternate results, and referring now to FIG. 11, the alternate results display area 1110 displays a closed menu of alternate results for that item as well. Referring now to FIG. 12, once the user has included the desired data from the EMR, the user can select to save the case report form by selecting the button in the save display area 1210. A visual indication 1220, 1230 is also provided when alternate results are available. In one embodiment, the appearance of a value is modified (e.g., italicized) to provide the visual indication.

Referring now to FIG. 13, the case report form includes a source audit display area 1310 that displays audit information associated with the data from the source system. The case report form also includes a form audit display area 1320, 1330 that displays audit information associated with the case report form. As can be appreciated, the form audit display area allows a change history for the case report form. For example, the original data was saved to the integrated data capture system with its associated audit information and is displayed in the first form audit display area 1330. A user may then change the data within the case report form to alternate data. The changed data is saved to the integrated data capture system with its associated audit information and displayed in the second form audit display area 1320. This change history allows a user to reconstruct the item's full history including when it was saved in the source system by mapping a result from the case report form to its origin in the EMR which is particularly useful when a result is documented more than once in the source system. An auditor is able to identify exactly which result is the one that was captured and saved into the case report form.

Figure 14:
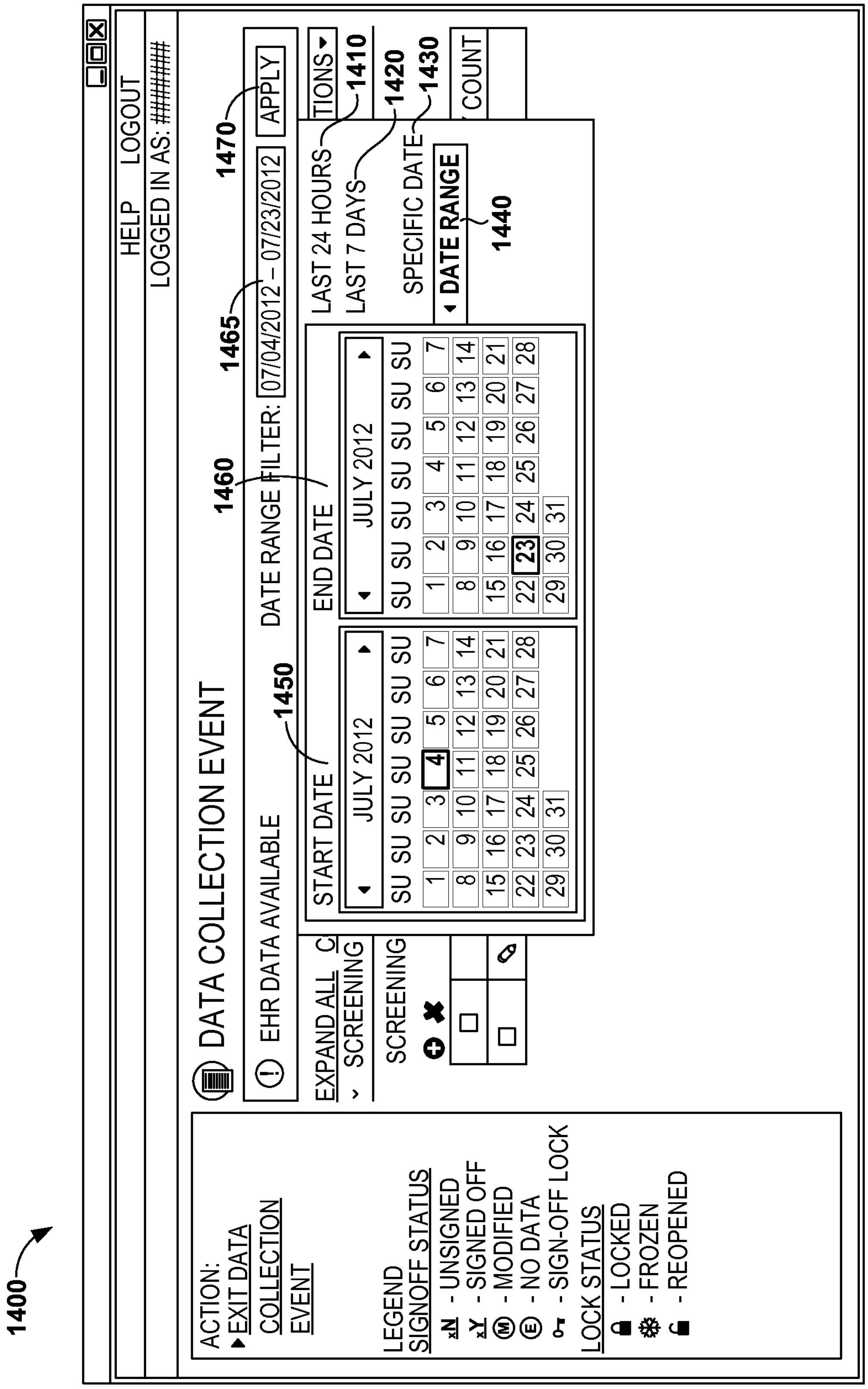

Referring now to FIG. 14, the availability of data can be manipulated to select time-specific data to include in the case report form. For example, in one embodiment, available data from the last twenty-four hours 1410 can be selected as a filter. In another embodiment, available data from the last seven days 1420 can be selected as a filter. In another embodiment, available data from a specific data 1430 can be selected as a filter. In another embodiment, available data from a data range 1440 can be selected as a filter. In the date range example, a start date 1450 and end date 1460 is selected for the date range filter 1465. Once the desired filter is selected, an apply button 1470 is selected to apply the filter to the available data.

Figure 15:
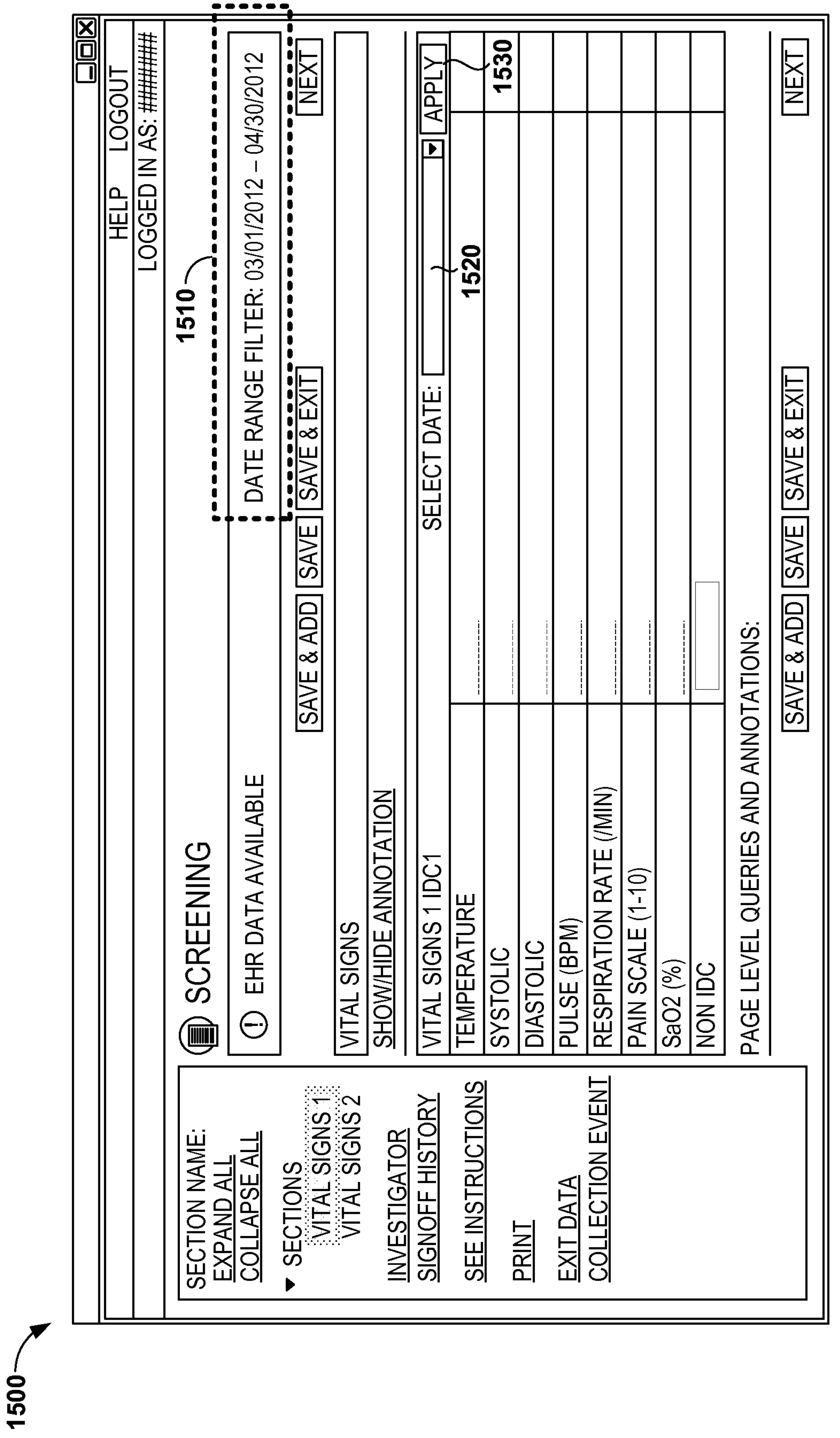

Referring now to FIG. 15, the selected date range 1510 is displayed within the case report form. As discussed, the selected data range impacts availability of data for the alternate results. A date 1520 can be selected within the selected date range 1510 and once the apply button 1530 is selected, the case report form is populated with the alternate result for the date 1520.

As can be understood, the present invention provides systems, methods, and user interfaces for integrated data capture. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. Non-transitory computer storage media having computer-executable instructions embodied thereon, that when executed by one or more computing devices, cause the one or more computing devices to perform a method for populating case report forms during integrated data capture, the method comprising:

receiving a selection of a plurality of data items from an Electronic Medical Record (EMR), the plurality of data items to be associated with one another for integrated data capture;

assigning a first data item of the plurality of data items as an item group key, the item group key having at least a second data item of the plurality of data items chronologically related thereto;

gathering, from the EMR, a first recorded value and a second recorded value for the item group key;

presenting, in association with a case report form having unpopulated fields for the first data item and the second data item, an indicator indicating that multiple values for the item group key are available within the EMR;

receiving a selection of the indicator;

based upon the receiving of the selection of the indicator, presenting a closed menu having the first recorded value and the second recorded value for the item group key;

receiving a selection of one of the first recorded value and the second recorded value for the item group key; and populating the field of the case report form for the first data item with the selected value for the item group key, and automatically populating the field of the case report form for the second data item with a corresponding value for the second data item;

wherein manual updates for at least the item group key and the second data item are not allowed.

2. The media of claim 1, further comprising initiating an integrated data capture workflow from within the EMR.

3. The media of claim 2, further comprising gathering data from the EMR to make available to the case report form.

4. The media of claim 1, wherein, the value for the second data item includes a name of a person who documented the second recorded value for the item group key in the EMR and a date and time associated with the second recorded value.

5. The media of claim 1, further comprising receiving manual entry of contextual information for the second recorded value.

6. The media of claim 1, wherein the integrated data capture includes a particular protocol selected by a user.

7. The media of claim 6, further comprising creating a case report utilizing the case report form and the protocol.

8. The media of claim 1, further comprising receiving a selection of a date range.

9. The media of claim 1, further comprising receiving a selection to clear unwanted data for the case report form.

10. The media of claim 1, further comprising receiving audit information from the EMR for a case report form audit trail.

11. The media of claim 1, further comprising receiving audit information for the case report form, wherein the audit information comprises a change reason only if an alternate value is selected and the alternate value selected is replacing a portion of data previously saved in the case report form.

12. A computer system that facilitates populating case report forms during integrated data capture, the computer system comprising a processor coupled to a computer storage medium, the computer storage medium having stored thereon a plurality of computer software components executable by the processor, the computer software components comprising:

a group component that receives a selection of a plurality of data items from an Electronic Medical Record (EMR), the plurality of data items to be associated with one another for integrated data capture;

an assignment component that assigns a first data item of the plurality of data items as an item group key, the item group key having at least a second data item of the plurality of data items chronologically related thereto;

a gather component that gathers, from the EMR, a first recorded value and a second recorded value for the item group key;

an indicator component that presents, in association with a case report form having unpopulated fields for the first data item and the second data item, an indicator that indicates that multiple values for the item group key are available within the EMR;

a selection component that receives a selection of the presented indicator;

a presentation component that, based upon the receiving of the selection of the indicator, presents a closed menu having the first recorded value and the second recorded value for the item group key;

wherein the selection component further receives a selection of one of the first recorded value and the second recorded value for the item group key; and a population component that populates the field of the case report form for the first data item with the selected value for the item group key, and automatically populates the field of the case report form for the second data item with a corresponding value for the second data item;

wherein manual updates for at least the item group key and the second data item are not allowed.

13. The system of claim 12, comprising a mapping component that allows a user to define a protocol such that additional case report forms can be created using the same protocol.

14. The system of claim 12, further comprising an audit component for adding audit information from the EMR for the second recorded value.

15. The system of claim 12, further comprising a clear component for receiving a selection to clear unwanted data from the case report form.

16. The system of claim 12, further comprising a submit component for submitting the case report form.

* * * * *